United States Patent
Bloch et al.

(12)

(10) Patent No.: US 6,331,618 B1
(45) Date of Patent: Dec. 18, 2001

(54) COMPOSITIONS OF SOLVENTS AND HIGH CONCENTRATIONS OF NUCLEIC ACID ANALOGS

(75) Inventors: William Bloch, San Mateo; William E. Werner, San Carlos, both of CA (US); Michael Egholm, Wayland; Rene L. Myers, Framingham, both of MA (US)

(73) Assignee: PE Corporation (NY), Foster City, CA (US)

( * ) Notice: Subject to any disclaimer, the term of this patent is extended or adjusted under 35 U.S.C. 154(b) by 0 days.

(21) Appl. No.: 09/311,079

(22) Filed: May 13, 1999

(51) Int. Cl.[7] .................................................. C07H 21/00
(52) U.S. Cl. ..................... 536/25.4; 536/4.1; 536/22.1; 536/23.1; 536/25.41; 530/300; 530/333; 530/350; 544/116; 544/218
(58) Field of Search .................... 536/22.1, 23.1, 536/25.4, 25.41, 4.1; 530/300, 333, 350; 554/116, 218

(56) References Cited

U.S. PATENT DOCUMENTS

| 4,146,454 | * | 3/1979 | Haber . |
| 5,034,506 | | 7/1991 | Summerton et al. . |
| 5,539,082 | * | 7/1996 | Nielsen et al. . |
| 5,852,083 | | 12/1998 | Walsh et al. . |
| 6,015,887 | * | 1/2000 | Teng . |

FOREIGN PATENT DOCUMENTS

| 197 12 530 | 10/1998 | (DE) . |
| 0 672 700 | 9/1995 | (EP) . |
| WO 98/41531 | 9/1998 | (WO) . |

OTHER PUBLICATIONS

International Search Report dated Oct. 26, 2000 in PCT/US 00/13227.

Uhlmann and Peyman, "Oligonucleotide Analogs Containing Dephospho–Internucleoside Linkages." *Methods in Molecular Biology* 20:355–389 (1993).

Reichardt, Christian, "Solvents and Solvent Effects in Organic Chemistry," VCH, 2nd Edition., Weinheim, Germany, pp. 407–410 (1988).

Egholm et al., "PNA hybridizes to complementary oligonucleotides obeying the Watson–Crick hydrogen–bonding rules," *Nature* 365:566–568 (Oct. 7, 1993).

Schmidt et al., "Separation of "Uncharged" Oligodeoxynucleotide Analogs by Anion–Exchange Chromatography at High pH," *Analytical Biochemistry* 235:239–240 (1996).

Gildea et al., "PNA Solubility Enhancers," *Tetrahedron Letters* 39:7255–7258 (1998).

* cited by examiner

*Primary Examiner*—James O. Wilson
(74) *Attorney, Agent, or Firm*—Alex Andrus

(57) ABSTRACT

The invention provides compositions and methods suitable for dissolving nucleic acid analogs with uncharged, neutral backbones at high concentrations at approximately neutral pH. By using the compositions of the invention, which include a polar, aprotic solvent, concentrations of nucleic acid analogs such as PNA can be achieved in the range of approximately 1 $\mu$M to 10 mM.

24 Claims, No Drawings

SEQUENCE LISTING

```
<160> NUMBER OF SEQ ID NOS: 6

<210> SEQ ID NO 1
<211> LENGTH: 15
<212> TYPE: DNA
<213> ORGANISM: Unknown
<220> FEATURE:
<223> OTHER INFORMATION: Test Sequence

<400> SEQUENCE: 1
aggtcaacga gcaag                                              15

<210> SEQ ID NO 2
<211> LENGTH: 12
<212> TYPE: DNA
```

-continued

```
<213> ORGANISM: Unknown
<220> FEATURE:
<223> OTHER INFORMATION: Test Sequence

<400> SEQUENCE: 2 ggaggggggaa ga                                                         12

<210> SEQ ID NO 3
<211> LENGTH: 15
<212> TYPE: DNA
<213> ORGANISM: Unknown
<220> FEATURE:
<223> OTHER INFORMATION: Test Sequence

<400> SEQUENCE: 3
ctttccttca ctgtt                                                       15

<210> SEQ ID NO 4
<211> LENGTH: 15
<212> TYPE: DNA
<213> ORGANISM: Unknown
<220> FEATURE:
<223> OTHER INFORMATION: Test Sequence

<400> SEQUENCE: 4
ctttcctcca ctgtt                                                       15

<210> SEQ ID NO 5
<211> LENGTH: 15
<212> TYPE: DNA
<213> ORGANISM: Unknown
<220> FEATURE:
<223> OTHER INFORMATION: Test Sequence

<400> SEQUENCE: 5
aggtcaacga gcaag                                                       15

<210> SEQ ID NO 6
<211> LENGTH: 12
<212> TYPE: DNA
<213> ORGANISM: Unknown
<220> FEATURE:
<223> OTHER INFORMATION: Test Sequence

<400> SEQUENCE: 6
ccaaagatga ta                                                          12
```

US 6,331,618 B1

COMPOSITIONS OF SOLVENTS AND HIGH CONCENTRATIONS OF NUCLEIC ACID ANALOGS

FIELD OF THE INVENTION

The invention relates generally to the field of nucleic acid analogs with uncharged, neutral backbones. Specifically, this invention is directed to aqueous mixtures of polar aprotic solvents that enable high-concentration dissolution of peptide nucleic acids (PNA).

REFERENCES

Alberts, B., Bray, D., Lewis, J., Raff, M., Roberts, K. and Watson, J. "Molecular Biology of the Cell, Second Edition", Garland Publishing, Inc., New York, 1989.

Andrus, A. "Chemical methods for 5' non-isotopic labelling of PCR probes and primers" (1995) in PCR 2: A Practical Approach, Oxford University Press, Oxford, pp. 39–54.

Atkins, P. W. "Physical Chemistry", W. H. Freeman and Co., San Francisco, Calif., 1978, pp. 746.

Beaucage, S. and Iyer, R. "Advances in the synthesis of oligonucleotides by the phosphoramidite approach", Tetrahedron 48:2223–2311 (1992).

Blackburn, G. and Gait, M. Eds. "DNA and RNA structure" in Nucleic Acids in Chemistry and Biology, $2^{nd}$ Edition, (1996) Oxford University Press, pp. 15–81.

Blanchard, Alan P. "Solvent for biopolymer synthesis, solvent microdroplets and apparatus employing inkjet pump for automated solid-phase synthesis of biopolymers" PCT Int. Appl., WO 9841531, Intl. publication date Sep. 24, 1998.

Buchardt, O., Egholm, M., Nielsen, P., and Berg, R. "Peptide Nucleic Acids", WO 92/20702, Intl. Pub. Date Nov. 26, 1992.

Caruthers, M. and Beaucage, S. "Phosphoramidite compounds and processes", U.S. Pat. No. 4,415,732, issued Nov. 15, 1983.

Caruthers, M. and Matteucci, M. "Process for preparing polynucleotides", U.S. Pat. No. 4,458,066, issued Jul. 3, 1984.

CRC Handbook of Chemistry and Physics, 63rd Edition, Weast, R. C., Editor, CRC Press, Inc., Boca Raton, Fla., pp. E-59–62.

Dueholm, K., Egholm, M., Behrens, C., Christensen, L., Hansen, H., Vulpius, T., Petersen, K., Berg, R., Nielsen, P. and Buchardt, O. "Synthesis of peptide nucleic acid monomers containing the four natural nucleobases: thymine, cytosine, adenine, and guanine and their oligomerization", J. Org. Chem. 59:5767–73 (1994).

Egholm, M., Buchardt, O., Christensen, L., Behrens, C., Freier, S., Driver, D., Berg, R. and Kim, S. "PNA hybridizes to complementary oligonucleotides obeying the Watson-Crick hydrogen bonding rules", Nature 365:566–68 (1993).

Englisch, U. and Gauss, D. "Chemically modified oligonucleotides as probes and inhibitors", Angew. Chem. Int. Ed. Engl. 30:613–29 (1991).

Gildea, B., Casey, S., MacNeill, J., Perry-O'Keefe, H., Sorensen, D and Coull, J. "PNA solubility enhancers", Tetrahedron Letters 39:7255–58 (1998).

Goodnow, R. and Tam, S. "Antisense Oligomers", U.S. Pat. No. 5,780,607, issued Jul. 14, 1998.

Hermanson, G. in Bioconjugate Techniques (1996) Academic Press, San Diego, pp. 40–55, 643–671.

Kricka, L. in Nonisotopic DNA Probe Techniques (1992), Academic Press, San Diego, pp. 3–28.

Kutyavin, I., Lukhtanov, E., Gamper, H. and Meyer, R. "Covalently linked oligonucleotide minor groove binder conjugates", WO 96/32496, Intl. Publ. Date Oct. 17, 1996.

Lee, L., Spurgeon, S., Rosenblum, B. "Energy transfer dyes with enhanced fluorescence", U.S. Pat. No. 5,800,996, issued Sep. 1, 1998.

Livak, K., Flood, S. and Marmaro, J. "Method for Detecting Nucleic Acid Amplification Using Self-Quenching Fluorescence Probe", U.S. Pat. No. 5,538,848, issued Jul. 23, 1996.

Livak, K., Flood, S., Marmaro, J. and Mullah, K. "Self-quenching fluorescence probe", U.S. Pat. No. 5,723,591, issued Mar. 3, 1998.

McMurry, J. Organic Chemistry (1984) Brooks/Cole Publishing Co., Monterey, Calif., pp. 313–15.

Menchen, S., Lee, L., Connell, C., Hershey, N., Chakerian, V., Woo, S. and Fung, S. "4,7-Dichlorofluorescein dyes as molecular probes", U.S. Pat. No. 5,188,934, issued Feb. 23, 1993.

Meyer, R. "Incorporation of modified bases in oligonucleotides" in Protocols for Oligonucleotide Conjugates, Ed. S. Agrawal (1994) Humana Press, Totowa, N.J., pp. 73–92.

Miller, P. and Ts'O, P. "Synthesis of oligo-2'-deoxyribonucleoside methylphosphonates" in Oligonucleotides and Analogues, Ed. F. Eckstein (1991) IRL Press, Oxford.

Nielsen, P., Egholm, M., Berg, R. and Buchardt, O. "Sequence-selective recognition of DNA by strand displacement with a thymidine-substituted polyamide", Science 254:1497–1500 (1991).

Oliver, R., Ed. "HPLC of Macromolecules, A Practical Approach, 2nd Edition", Oxford University Press, Oxford, (1999).

Reichardt, C. Solvents and Solvent Effects in Organic Chemistry, 2nd Edition, VCH mbH, Weinheim, Germany (1990), pp. 407–411.

Rickwood, D. and Hames, B. Eds. "Gel Electrophoresis of Nucleic Acids, A Practical Approach, 2nd Edition", Oxford University Press, Oxford (1990).

Schmidt, J., Nielsen, P., and Orgel, L. "Separation of "Uncharged"oligodeoxynucleotide analogs by anion-exchange chromatography at high pH", Analytical Biochemistry 235:239–41 (1996).

Summerton, J. and Weller, D. "Uncharged morpholino-based polymers having achiral intersubunit linkages", U.S. Pat. No. 5,034,506, issued Jul. 23, 1991.

Summerton, J. and Weller, D. "Sequence-specific binding polymers for duplex nucleic acids", U.S. Pat. No. 5,405,938, issued Apr. 11, 1995.

Tyagi, S. and Kramer, F. "Molecular Beacons: Probes that fluoresce upon hybridization", Nature Biotechnology, 14:303–08 (1996).

Van der Laan, A., Brill, R., Kuimelis, R., Kuyl-Yeheskiely, E., van Boom, J., Andrus, A. and Vinayak, R. "A convenient automated solid-phase synthesis of PNA-(5')-DNA-(3')-PNA chimera", Tetrahedron Lett. 38:2249–52 (1997).

Vinayak, R., van der Laan, A., Brill, R., Otteson, K., Andrus, A., Kuyl-Yeheskiely, E. and van Boom, J. "Automated chemical synthesis of PNA-DNA chimera on a nucleic synthesizer", Nucleosides & Nucleotides 16:1653–56 (1997).

Walsh, W. and Waldrop, M. "Process for making hot-melt adhesives using water-soluble substituted lactam/polymer solutions as feedstocks", U.S. Pat. No. , 5,852,083.

BACKGROUND

Nucleic acid analogs, including peptide nucleic acids (PNA), internucleotide analogs, and nucleobase analogs, are often studied and characterized by analytical tests and methods at substantially higher concentrations than physiological concentrations under metabolic conditions (Alberts, 1989). Some tests, methods and experiments that may require high concentrations of nucleic acid analogs are intracellular antisense inhibition of transcription and translation of sense DNA and mRNA, labelling of nucleic acid analog reactions, and attaching nucleic acid analogs to surfaces of other heterogeneous media. Analytical methods that may require high concentrations of nucleic acid analogs are gel electrophoresis (Rickwood, 1990), high-performance liquid chromatography (HPLC) (Oliver, 1998), primer extension reactions, polymerase chain reaction (PCR), mass spectroscopy, nuclear magnetic resonance (NMR) and X-ray crystallization.

Nucleic acid analogs with uncharged, neutral backbones, such as peptide-nucleic acids (PNA) (Buchardt, 1992), morpholino-carbamate (Summerton, 1991), methyl phosphonate oligonucleotides (Miller, 1991), and others (Goodnow, 1998) have the advantage of nuclease-resistance for prolonged in vivo stability but are notoriously difficult to solubilize and maintain in aqueous solution, particularly at neutral pH. Such uncharged analogs lack the solubility-facilitating phosphate anions of DNA and RNA. PNA sequences with a N-(2-aminoethyl)-glycine polymer backbone and high purine nucleobase content can be especially difficult to solubilize (Nielsen, 1991). Useful concentrations of PNA sequences with contiguous thymidine nucleobases are also sometimes difficult to achieve. Typically, PNA are dissolved in low pH, primarily aqueous solutions. PNA nucleobases are basic and become protonated and charged at low pH, increasing their solubility under acidic conditions. For the most part, nucleic acid analogs such as PNA are not appreciably soluble in neutral, aqueous conditions. If solution is achieved at neutral pH by elevated temperature, agitation, or other techniques, nucleic acid analogs are prone to precipitation when allowed to stand at or below room temperature. Furthermore, high concentrations of PNA and other nucleic acid analog molecules can aggregate to form insoluble, secondary and tertiary structures that precipitate from solution. These precipitates are often difficult to redissolve.

Aggregation of PNA and other nucleic acid analogs is a significant hindrance to purification, analysis, characterization, measurement, and use of these compounds (Schmidt, 1996). Insolubility and precipitation make the nucleic acid analog concentrations questionable and sample handling and storage unreliable. These limitations are unfortunate because solutions of high concentrations of nucleic acid analogs, e.g. purine-rich PNA are very desirable.

Nucleic acid analogs, such as PNA, are often covalently labelled, or conjugated, with hydrophobic labelling reagents for detection, affinity, or other recognition purposes in labelling reactions, e.g. fluorescent dyes, biotin, digoxigenin. Preferred labelling reaction conditions include aqueous, neutral solutions with high concentrations of the nucleic acid analog and the labelling reagents. Methods or compositions to attain high concentrations of nucleic acid analogs for labelling reactions are desirable.

The labelled nucleic acid analog conjugates that result from labelling reactions are often insoluble in neutral aqueous media. Methods or compositions to attain high concentrations of labelled nucleic acid analog conjugates, e.g. fluorescent dye-PNA, are desirable.

Nucleic acid analog mixtures with a propensity to precipitate, or that demonstrate insolubility, require onerous monitoring of their concentrations for appropriate experimental control. Sometimes dissolution of nucleic acid analogs with basic moieties that become protonated can be achieved at low pH, e.g. 1–5. However, not all tests, methods, experiments, applications or uses for nucleic acid analogs are feasible at acidic pH. For example, nucleic acids may not hybridize with specificity and affinity at acidic pH. In addition, there are several cell biological and molecular applications in which neutral pH is required or preferred (Alberts, 1989).

Certain labels and linkers have been covalently attached to nucleic acid analogs to enhance their solubility in attempts to attain high concentrations for various purposes. For example, hydrophilic moieties such as polyoxyethylene moieties have been conjugated to PNA to improve its solubility (Gildea, 1998). Attaching such solubilizing moieties requires special reagents and extra expense to attain high concentration nucleic acid analog solutions. An additional drawback is the adverse impact on overall synthesis efficiency when attaching solubilizing moieties. Furthermore, such moieties may change the shape, charge, hydrophobicity, and other properties of a nucleic acid analog. Attached moieties may disrupt, prevent, or impair biological utility of the nucleic acid analog function, e.g. hybridization specificity or affinity, antibody/antigen recognition, and enzymatic activity.

Solubility properties of nucleic acid analogs are difficult to predict, and are type and sequence dependent. Therefore, it is desirable to provide solvents and solvent mixtures capable of solubilizing nucleic acid analogs at high concentrations. Conditions which allow long term storage, i.e. one week or more, of nucleic acid analogs such as PNA at $\mu$M ($10^{-6}$ molar,) to 10 mM ($10^{-2}$ molar) concentrations at neutral pH with retention of the PNA in solution are especially desirable.

SUMMARY

These and other shortcomings in the art are overcome by the present invention, which provides methods and novel compositions pertaining to high concentrations of nucleic acid analogs dissolved in solutions comprising polar aprotic solvents at approximately neutral pH.

In a first aspect of the invention, an aqueous composition comprises a nucleic acid analog with an uncharged, neutral backbone and about 5% to about 95% (v/v) of a polar aprotic solvent, wherein the concentration of the nucleic acid analog is in the range of about 1 $\mu$M to about 10 mM and the composition has a pH in the range of about 5 to about 9. Preferably the concentration of polar aprotic solvent is 10% to 60% (v/v). Preferably the composition has a pH in the range of 6 to 8.

The nucleic acid analog has an uncharged, neutral backbone. Preferably the nucleic acid analog is a PNA.

While any number of polar, aprotic solvents may be used, typically the polar, aprotic solvent is selected from the group consisting of:

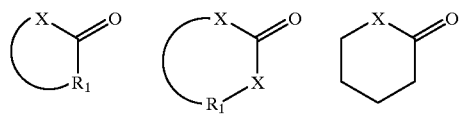

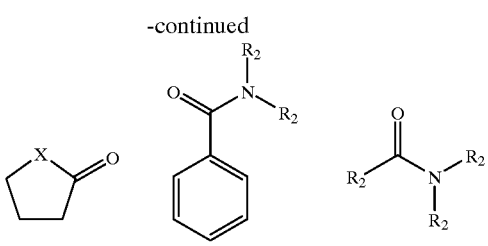

where X is O, NH, or NR$_2$; R$_1$ is alkyldiyl; and each R$_2$ is independently, methyl, cycloalkyl, alkyl, or aryl.

Preferred polar aprotic solvents have lactam, carbamate, urea, and carbonate functionality (Blanchard, 1998). A preferred polar aprotic solvent is NMP (Walsh, 1998). Preferably, NMP is in the range of 10% to 60% (v/v) concentration. Most preferably, the NMP is in the range of 40% to 60% (v/v) concentration of the composition.

The nucleic acid analog solution may optionally contain salts, typically at concentrations of, up to and including, 1M to assist solubility and/or to approximate metabolic, physiological, or other experimental conditions. Virtually any salt can be used, as long as it is soluble in the composition at the desired concentration. Thus, the salt can be inorganic salt, such as an alkali or alkaline earth halide (e.g. NaCl, KCl, MgCl$_2$, etc.) or it may be an organic salt, such as guanidinium chloride, guanidinium thiocyanate, sodium acetate, sodium formate, ammonium formate, tetrabutylammonium formate, triethylammonium acetate, and triethylammonium formate.

In a second aspect, a method of making a high concentration nucleic acid analog solution is provided, comprising the steps of: dissolving a nucleic acid analog with an uncharged, neutral backbone to a final concentration in the range of about 1 $\mu$M to 10 mM in an aqueous solvent system comprising about 5% to 95% (v/v) of a polar aprotic solvent at a pH in a range of about 5 to about 9. Optionally, the solution contains an acid or base, e.g. tris(hydroxymethyl)aminomethane (Tris) to adjust the pH. Preferably the nucleic acid analog is a PNA.

The invention provides stable formulations, such as kit components and custom nucleic acid analogs. In addition, it may allow for the development of new molecular and cellular applications for nucleic acid analogs and allow manipulation and chemical conjugation of PNA to other moieties using neutral reaction conditions. Also, this discovery may result in improved purification of PNA and ease in handling of these molecules. Furthermore, the invention provides high-concentration nucleic acid analog labelling reactions at, or near, neutral pH.

DETAILED DESCRIPTION OF THE PREFERRED EMBODIMENTS

Reference will now be made in detail to the preferred embodiments of the invention. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

I. Definitions

Unless stated otherwise, the following terms and phrases as used herein are intended to have the following meanings:

"Nucleoside" refers to a compound consisting of a purine, deazapurine, or pyrimidine nucleobase, e.g., adenine, guanine, cytosine, uracil, thymine, deazaadenine, deazaguanosine, and the like, linked to a pentose at the 1'-position.

"Nucleotide" refers to a phosphate ester of a nucleoside, e.g., a triphosphate ester, wherein the most common site of esterification is the hydroxyl group attached to the C-5 position of the pentose.

The terms "nucleic acid" or "oligonucleotide" mean polymers of nucleotide monomers, including double and single stranded deoxyribonucleotides, ribonucleotides, $\alpha$-anomeric forms thereof, and the like. The oligonucleotide may be composed entirely of deoxyribonucleotides, entirely of ribonucleotides, or mixtures thereof. The monomers are linked by internucleotide phosphodiester bond linkages, and associated counterions, e.g., H$^+$, NH$_4^+$, Na$^+$. Oligonucleotides typically range in size from a few monomeric units, e.g. 5–40, to several thousands of monomeric units. Whenever an oligonucleotide is represented by a sequence of letters, such as "ATGCCTG," it will be understood that the nucleotides are in 5'to 3' order from left to right and that "A" denotes deoxyadenosine, "C" denotes deoxycytidine, "G" denotes deoxyguanosine, and "T" denotes thymidine, unless otherwise noted.

The term "nucleic acid analogs" refers to analogs of nucleic acids comprising one or more nucleotide analog units, and possessing some of the qualities and properties associated with nucleic acids, e.g. Watson/Crick, wobble, and Hoogsteen base pairing, and other sequence recognition effects. Nucleic acid analogs may have modified nucleobase moieties, modified sugar moieties, and/or modified internucleotide linkages (Englisch, 1991). Modifications include labels. A preferred class of nucleic acid analogs is where the internucleotide moiety is modified to be neutral and uncharged at or near neutral pH, such as phosphoramidate, phosphotriester, and methyl phosphonate oligonucleotides where one of the non-bridging oxygen atoms is replaced by a neutral substituent, e.g. —NR$_2$,—OR, R. Another preferred class of nucleic acid analogs is where the sugar and internucleotide moieties have been replaced with an uncharged, neutral amide backbone, such as morpholino-carbamate and peptide nucleic acids (PNA). A preferred form of PNA is a N-(2-aminoethyl)-glycine amide backbone polymer (Nielsen, 1991). Whenever a PNA sequence is represented, it is understood that the amino terminus is at the left side and the carboxyl terminus is at the right side.

The term "Watson/Crick base-pairing" refers to a pattern of specific pairs of nucleotides, and analogs thereof, that bind together through sequence-specific hydrogen-bonds, e.g. A pairs with T and U, and G pairs with C.

"Polar aprotic solvent" refers to an organic solvent having a dipole moment of about 2 debye units or more (Atkins, 1978; CRC Handbook, 1982; Reichardt, 1990), a water solubility of at least about 5% (volume) at or near ambient temperature, i.e. about 20 ° C., and which does not undergo hydrogen exchange at approximately neutral pH i.e. in the range of 5 to 9, and preferably in the range of 6 to 8.

"Attachment site" refers to a site to which is covalently attached a linker.

"Linker" refers to one or more atoms connecting an oligonucleotide or nucleic acid analog to a label, or a solid-support through a covalent bond.

"Chimera" refers to an oligonucleotide or nucleic acid analog which includes one or more nucleotide and one or more nucleotide analog units.

"Conjugate" refers to a composition of a nucleic acid analog and a label whereby the label is covalently attached to the nucleic acid analog through a linker at an attachment site on the nucleic acid analog.

"Alkyl" refers to a saturated or unsaturated, branched, straight-chain, branched, or cyclic hydrocarbon radical derived by the removal of one hydrogen atom from a single carbon atom of a parent alkane, alkene, or alkyne. Typical alkyl groups include, but are not limited to, methyl, ethyl, propyl, butyl, and the like. In preferred embodiments, the alkyl groups consist of 1–12 saturated and/or unsaturated carbons.

"Cycloalkyl" refers to a cyclic alkyl radical. Nitrogen atoms with cycloalkyl substituents may form aziridinyl, azetidinyl, pyrrolidinyl, piperidinyl, larger rings, and substituted forms of heterocycles thereof.

"Alkyldiyl" refers to a saturated or unsaturated, branched, straight chain or cyclic hydrocarbon radical having two monovalent radical centers derived by the removal of one hydrogen atom from each of two different carbon atoms of a parent alkane, alkene or alkyne. Typical alkyldiyl radicals include, but are not limited to, ethyldiyl (—CH$_2$CH$_2$—), propyldiyl (—CH$_2$CH$_2$CH$_2$—), butyldiyl (—CH$_2$CH$_2$CH$_2$CH$_2$—), and the like.

"Aryl" refers to an unsaturated cyclic or polycyclic hydrocarbon radical having a conjugated resonance electron system. Typical aryl groups include, but are not limited to, radicals derived from phenyl, substituted phenyl, naphthalene, anthracene, biphenyl, and the like.

"Label" refers to any moiety covalently attached to an oligonucleotide that imparts a desired functionality or property (Hermanson, 1996). A preferred class of labels provides a signal for detection, e.g. fluorescence, chemiluminescence, and electrochemical luminescence (Kricka, 1992). Detection labels include, but are not limited to, fluorescent dyes (Menchen, 1993), such as fluorescein and rhodamine derivatives and resonance-energy transfer pairs (Livak, 1998; Livak, 1996; Tyagi, 1996), cyanine dyes, chemiluminescent dyes and energy-transfer dyes (Lee, 1998). Another preferred class of labels serve to enhance, stabilize, or influence hybridization and base pairing interactions, e.g. intercalators, minor-groove binders (Kutyavin, 1996), and cross-linking functional groups (Blackburn, 1996). Yet another preferred class of labels serve to effect the separation or immobilization of a labelled nucleic acid analog by specific or non-specific capture means, e.g. biotin, 2, 4-dinitrophenyl (DNP), and digoxigenin (Andrus, 1995).

II. Polar Aprotic Solvents

Polar aprotic solvents are useful for dissolving nucleic acid analogs. Homogeneous, approximately neutral pH, stable solutions of nucleic acid analogs at high-concentration can be achieved with aqueous compositions comprising polar aprotic solvents. Polar aprotic solvents improve the solubility of PNA at approximately neutral pH. The solubility of PNA correlates generally with increasing concentration of polar aprotic solvent, e.g. 5% to 90% of the total volume of the composition. Preferred concentrations of polar aprotic solvents are 10–60% (v/v), and most preferred is approximately 50% (v/v).

While any number of polar, aprotic solvents may be used, typically the polar, aprotic solvent is selected from the group consisting of:

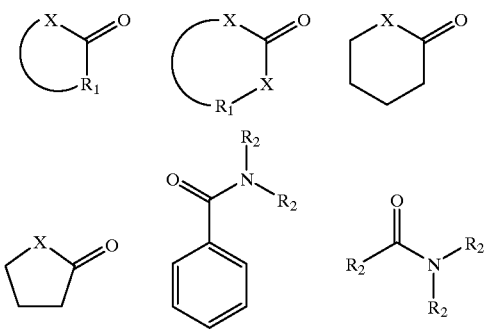

where X is O, NH, or NR$_2$; R$_1$ is alkyldiyl; and each R$_2$ is independently, methyl, cycloalkyl, alkyl, or aryl.

Preferred polar aprotic solvents include NMP, other N-alkyl pyrrolidinones, 2-pyrrolidone, ethylene carbonate, propylene carbonate, dimethylacetamide (DMA), N-methyl-2-piperidone, 2-piperidone, other N-alkyl piperidones, caprolactam, dimethylbenzamide, diethylbenzamide, other dialkylacetamides, and combinations thereof. Such compounds are distinguished by their relatively high dielectric constants, high dipole moments (Reichardt, 1990), and solubility in water (McMurry, 1984).

A preferred polar aprotic solvent is N-methyl pyrrolidinone (NMP) represented by the structure:

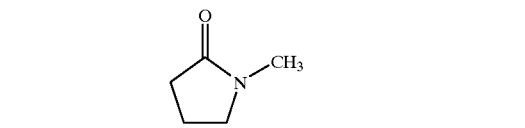

III. Salts

The salts may assist in solubilizing and maintaining the solubility and stability of the nucleic acid analog in the solution. Salt compounds are typically alkali metal or alkylammonium cations and halide or other anions. Preferred salts include sodium chloride, potassium chloride, guanidinium chloride, guanidinium thiocyanate, sodium acetate, sodium formate, ammonium formate, tris(hydroxymethyl) aminomethane hydrochloride (Tris-HCl), sodium phosphate, potassium phosphate, tetrabutylammonium formate, triethylammonium acetate, triethylammonium formate, and combinations thereof Preferred salts include Tris-HCl and sodium chloride. The salt may be present in the composition at a concentration up to 1 M. Preferably the salt is present between 0 to 0.1 M.

IV. Nucleic Acid Analogs

The aqueous compositions of the invention are suitable for solubilizing virtually any nucleic acid analog at high concentrations. Thus, the nucleic acid analogs may bear modifications to the nucleobase, sugar, and/or internucleotide moieties.

Preferred nucleobase analog modifications include but are not limited to C-5-alkyl pyrimidines, 2-thiopyrimidine, 2,6-diaminopurine, C-5-propyne pyrimidine, phenoxazine (Flanagan, 1999), 7-deazapurine, isocytidine, pseudo-isocytidine, isoguanosine, 4(3 H)-pyrimidone, hypoxanthine, 8-oxopurines and universal base (Meyer, 1994).

Preferred sugar analog modifications in one or more of the nucleosides include, but are not limited to, 2'- or 3'-modifications where the 2'- or 3'-position may be hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo.

Other preferred sugar analog modifications include 4'-α-anomeric nucleotides, 1'-α-anomeric nucleotides, 2'-branching group-ribonucleotides, and 2'-O-branching group-ribonucleotides.

Preferred modified internucleotide linkages which form neutral, uncharged backbones include, but are not limited to, replacing a non-bridging oxygen in the internucleotide phosphodiester linkage with substituted sulfur, oxygen, carbon, and nitrogen to form alkylphosphorothioate, alkylphosphotriester, alkylphosphonate, and phosphoramidate, respectively. Other preferred internucleotide analogs include; N-(2-aminoethyl) -glycine PNA, morpholino-carbamate (Summerton, 1991) and other uncharged, neutral backbones.

The compositions of the invention are particularly useful for dissolving PNA at high concentrations. Even PNA comprised of more than 50% purine nucleobases, which have proven to be extremely insoluble under standard assay and/or analytical conditions, can be solubilized at concentrations in the 1 μM to 10 mM range.

An especially preferred form of PNA that can be dissolved at high concentration according to the invention has an uncharged backbone of N-(2-aminoethyl)-glycine, a peptide-like unit (Egholm, 1993; Nielsen, 1991). PNA/DNA chimeras and labelled PNA are preferred variants of PNA in the practice of the present invention. PNA oligomers are capable of base-pairing with complementary sequences by Watson/Crick base-pairing with high affinity and specificity. PNA and PNA/DNA chimera can be synthesized using conventional methods on commercially available, automated synthesizers, with commercially available reagents (Dueholm, 1994; Vinayak, 1997; Van der Laan, 1997). PNA with a N-(2-aminoethyl)-glycine backbone has the structure:

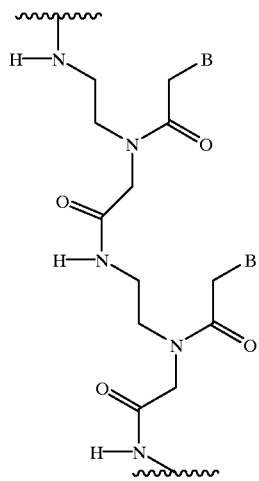

where B is a nucleobase or nucleobase analog.

Another amide-linked, uncharged nucleic acid analog that can be dissolved at high concentration according to the invention has morpholino-carbamate backbone units:

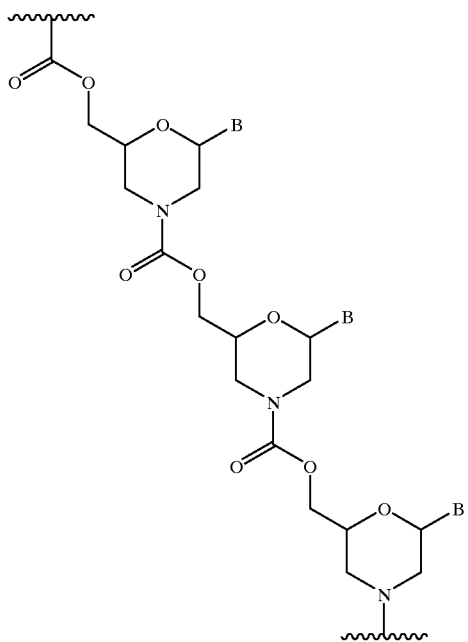

where B is a nucleobase or nucleobase analog (Summerton, 1995; Summerton, 1991).

A preferred nucleic acid analog solution is prepared by mixing a known amount of one or more nucleic acid analogs with known volumes and amounts of one or more polar aprotic solvents and water. The relative volume amounts in the solution of polar aprotic solvent and water may be 5 to 95 (v/v) % polar aprotic solvent and 5 to 95 volume % water. Preferably, 10 to 60 (v/v) % polar aprotic solvent is present. Most preferably, 40 to 60% (v/v) polar aprotic solvent is present. Salt may also be added to the solution, as a solid or pre-dissolved in water. The final concentration of the salt in the solution may be 0 to 1 molar. The vessel may be vortexed or otherwise agitated and/or heated at about 50° C. for about 1 to 15 minutes to help achieve solution. Acid or base sufficient to adjust the pH to a range of 5 to 9 is added before or after solution is achieved. A preferred pH range is 6 to 8, and a most preferred pH is approximately pH 7. For example, 2M Tris, may be added to a final concentration of about 0.1 mM to attain pH 8. The final concentration of the nucleic acid analog(s) may be in the range of about 1 μM to about 10 mM. Preferably, a high concentration of nucleic acid analog is achieved, 1 mM or more. A mixture of nucleic acid analogs may be in the solution. Solutions may be stored at ambient or sub-ambient temperatures.

PNA may be synthesized at the 2 μmole scale, using Fmoc/Bhoc, tBoc/Z, or MMT protecting group monomers on Expedite Synthesizer (PE Biosystems) on XAL or PAL support, on the Model 433A Synthesizer (PE Biosystems) on MBHA support, or on other automated synthesizers. After synthesis is complete, the crude PNA is cleaved from the support, e.g. with trifluoroacetic acid, and then precipitated with diethylether and washed twice in diethylether. PNA is purified by reverse-phase HPLC, analyzed by mass spectroscopy, and quantitated by correlating absorbance at 260 nm with mass. PNA/DNA chimeras (Van der Laan, 1997; Vinayak, 1997) may be synthesized with MMT protecting group PNA monomers and phosphoramidite nucleoside monomers (Beaucage, 1992).

V. EXAMPLES

The invention will be further clarified by a consideration of the following examples, which are intended to be purely exemplary of the present invention and not to limit its scope in any way.

Example 1

A high purine (73%) PNA sequence (SEQ. ID NO. 1) with 15 N-(2-aminoethyl)-glycine monomer units was synthesized with two solubility enhancing moieties, O (2-[2-(2-aminoethoxy]acetic acid) attached at the amino terminus:

| | |
|---|---|
| OO—AGG TCA ACG AGC AAG | SEQ. ID NO. 1 | was synthesized, cleaved, and purified. Two samples were aliquotted, each containing 59 nmole of SEQ. ID NO. 1, into in a 1.5 ml microcentrifuge tube and dried under vacuum. To sample 1, 29.5 μl NMP and 29.5 μl 0.1M Tris-HCl pH 8 were added. To sample 2, 59 μl of 0.05M Tris-HCl pH 8 was added. The maximum, targeted concentration of each tube was thus 1.0 mmole. The tubes were vortexed for about 1 minute. Sample 1 gave a clear solution. Sample 2 gave a turbid solution.

To measure concentrations, the samples were centrifuged at about 14,000×g in a microcentrifuge for about 10 minutes to sediment any insoluble nucleic acid analog or other impurities. A small aliquot of the solution was withdrawn, and diluted with a known volume of water. The absorbance was measured at 260 nm and correlated to mass. Sample 1, containing 50% NMP, gave a concentration of PNA of 0.69 mM, indicating 69% dissolution. Sample 2, containing no NMP, gave a concentration of PNA of 0.13 mM, indicating 13% dissolution.

Example 2

A homopurine sequence PNA (SEQ. ID NO. 2) with 12 N-(2-aminoethyl)-glycine monomer units was synthesized with solubility enhancing moieties, O (2-[2-(2-aminoethoxy]acetic acid) attached at the amino- and carboxy-terminii.

| | |
|---|---|
| OO-GGA GGG GGA AGA-OOO | SEQ. ID NO. 2 |

SEQ. ID NO. 2 was completely insoluble in water at neutral pH. Addition of 10% or 50% NMP brought the PNA immediately into solution at 1 mM. Both solutions remained homogeneous without precipitation over 2 months at room temperature. Two additional biotin labelled PNA sequences, SEQ. ID NO. 3 and 4, are also soluble at 1.0 mM in 50% NMP.

| | |
|---|---|
| Biotin-OO-CTT TCC TTC ACT GTT | SEQ. ID NO. 3 |
| Biotin-OO-CTT TCC TCC ACT GTT | SEQ. ID NO. 4 |
| Fluorescein-OO-AGG TCA ACG AGC AAG | SEQ. ID NO. 5 |
| Rhodamine-OO-CCA AAG ATG ATA | SEQ. ID NO. 6 |

Example 3

A group of four N-(2-aminoethyl)-glycine PNA samples were dissolved in compostions without (0% NMP) and with (50% NMP). The Target concentration is the maximum concentration, at which all the sample would be dissolved. The actual dissolved concentrations (mM) were measured by absorbance as in Example 1.

TABLE

Concentration (mM) of PNA in nucleic acid analog solvent compositions at room temperature

| SEQ. ID NO. | 0% NMP* | day | 50% NMP** | day | Target conc. | pH |
|---|---|---|---|---|---|---|
| 1 | 0.06 | 0 | 0.40 | 0 | 4.0 | 7 |
| 5 | 0.10 | 0 | 1.30 | 0 | 2.0 | 7 |
| 5 | 0.009 | 0 | 0.06 | 0 | 0.10 | 7 |
| 6 | 0.03 | 0 | 0.16 | 0 | | 7 |
| 4 | 0.70 | 0 | 1.0 | 0 | 1.0 | 8 |
| 4 | 0.30 | 3 | 1.0 | 3 | 1.0 | 8 |
| 4 | 0.30 | 14 | 1.0 | 14 | 1.0 | 8 |

*0.1 M Tris
**1:1 (v:v) NMP: 0.1 M Tris.

Although only a few embodiments have been described in detail above, those having ordinary skill in the molecular biology and chemistry arts will clearly understand that many modifications are possible in the preferred embodiment without departing from the teachings thereof. All such modifications are intended to be encompassed within the following claims.

We claim:

1. An aqueous composition comprising a nucleic acid analog with an uncharged, neutral backbone and about 5% (v/v) to about 95% (v/v) of a polar aprotic solvent, wherein the concentration of the nucleic acid analog is in the range of about 1 $\mu$M to about 10 mM and the composition has a pH in the range of about pH 5 to about pH 9; and wherein the polar aprotic solvent is selected from the group consisting of:

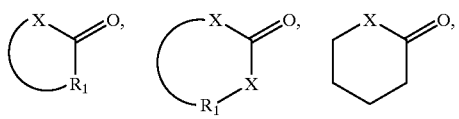

where X is O, NH, or $NP_2$; $R_1$ is alkyldiyl; and each $R_2$ is independently selected from the group consisting of methyl, cycloalkyl, alkyl, and aryl.

2. The aqueous composition of claim 1 wherein the polar aprotic solvent has a concentration in the range of about 10% to about 60% (v/v).

3. The aqueous composition of claim 1 which further comprises up to about 1 M salt.

4. The composition of claim 3 wherein the salt is selected from the group consisting of sodium chloride, potassium chloride, guanidinium chloride, guanidinium thiocyanate, sodium acetate, sodium formate, tetra-butylammonium formate, triethylammonium acetate, triethylammonium bicarbonate, and triethylammonium formate.

5. The composition of claim 1 wherein the solution further comprises acid or base sufficient to adjust the pH to a range of 6 to 8.

6. The aqueous composition of claim 1 wherein the polar aprotic solvent is selected from the group consisting of NMP, 2-pyrrolidone, ethylene carbonate, propylene carbonate, DMA, N-methyl-2-piperidone, 2-piperidone, caprolactam, dimethylbenzamide, and diethylbenzamide.

7. The aqueous composition of claim 6 wherein the polar aprotic solvent is NMP.

8. The aqueous composition of claim 7 wherein NMP has a concentration in the range of 10% to 60% (v/v).

9. The aqueous composition of claim 7 wherein NMP has a concentration in the range of 40% to 60% (v/v).

10. The aqueous composition of claim 1 wherein the nucleic acid analog comprises a PNA polymer.

11. The aqueous composition of claim 1 in which the nucleic acid analog is a PNA/DNA chimera.

12. The aqueous composition of claim 10 wherein the nucleic acid analog is N-(2-aminoethyl)-glycine PNA having the structure:

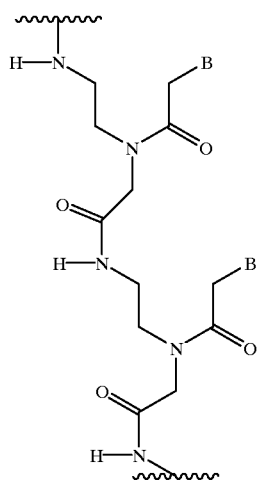

wherein B is a nucleobase or nucleobase analog.

13. The aqueous composition of claim 10 wherein the PNA has a purine nucleobase content in the range of 50% or higher.

14. A method of making a nucleic acid analog solution comprising
dissolving a nucleic acid analog with an uncharged, neutral backbone to a final concentration in the range of about 1 $\mu$M to 10 mM in an aqueous solvent system comprising about 5% to 95% (v/v) of a polar aprotic solvent; wherein the polar aprotic solvent is selected from the group consisting of:

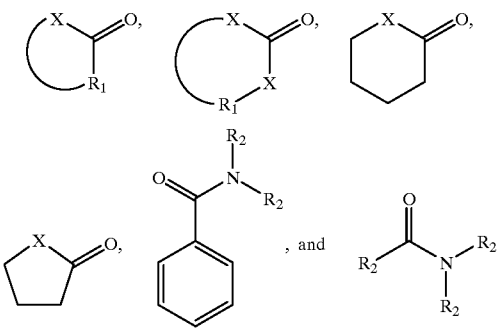

where X is O, NH, or $NR_2$; $R_1$ is alkyldiyl; and each $R_2$ is independently selected from the group consisting of methyl, cycloalkyl, alkyl and aryl; and
adjusting the pH to a range of about 5 to about 9.

15. The method of claim 14 wherein the nucleic acid analog comprises a PNA.

16. The method of claim 15 wherein the PNA is N-(2-aminoethyl)-glycine PNA.

17. The method of claim 14 wherein the polar aprotic solvent is NMP.

18. The aqueous composition of claim 12 wherein the PNA polymer comprises from 5 to 40 N-(2-aminoethyl)-glycine monomer units.

19. The aqueous composition of claim 18 wherein the PNA polymer further comprises one or more covalently attached 2-(2-aminoethoxy)acetic acid moieties.

20. The aqueous composition of claim 18 wherein the PNA polymer further comprises one or more labels wherein the labels are covalently attached to the PNA polymer and the labels are selected from fluorescent dyes, resonance-energy transfer pairs, energy-transfer dyes, intercalators, minor-groove binders, and cross-linking functional groups.

21. The aqueous composition of claim 20 wherein a label is covalently attached to the amino terminus of the PNA polymer.

22. The aqueous composition of claim 18 wherein the PNA polymer further comprises a fluorescein dye covalently attached to the PNA polymer.

23. The aqueous composition of claim 18 wherein the PNA polymer further comprises a rhodamine dye covalently attached to the PNA polymer.

24. The aqueous composition of claim 18 wherein the PNA polymer further comprises biotin covalently attached to the PNA polymer.

* * * * *